United States Patent [19]

Wijayarthna et al.

[11] Patent Number: 4,694,838
[45] Date of Patent: Sep. 22, 1987

[54] LOOP CORONARY CATHETER

[75] Inventors: Bandula Wijayarthna, Friendswood, Tex.; Glenn E. Newman, Durham, N.C.

[73] Assignees: Mallinckrodt, Inc., St. Louis, Mo.; Duke University, Durham, N.C.

[21] Appl. No.: 693,974

[22] Filed: Jan. 23, 1985

Related U.S. Application Data

[63] Continuation-in-part of Ser. No. 575,276, Jan. 30, 1984, abandoned.

[51] Int. Cl.[4] ............................................. A61M 25/00
[52] U.S. Cl. ...................................... 128/658; 604/281
[58] Field of Search ........................ 128/658, 657, 656; 604/8, 53, 55, 104, 264, 280, 281

[56] References Cited

U.S. PATENT DOCUMENTS

| | | | |
|---|---|---|---|
| 2,286,462 | 6/1942 | Chaffin | 604/43 |
| 2,492,384 | 12/1949 | Kaslow . | |
| 3,419,010 | 12/1968 | Williamson . | |
| 3,618,614 | 11/1971 | Flynn . | |
| 3,920,023 | 11/1975 | Dye et al. . | |
| 3,938,501 | 2/1976 | Erikson | 604/281 |
| 4,117,836 | 10/1978 | Erickson . | |
| 4,129,129 | 12/1978 | Amrine . | |
| 4,169,464 | 10/1979 | Obrez | 128/657 |
| 4,173,981 | 11/1979 | Mortensen . | |
| 4,212,304 | 7/1980 | Finney . | |
| 4,279,252 | 7/1981 | Martin | 604/280 |
| 4,531,933 | 7/1985 | Norton et al. | 604/8 |

OTHER PUBLICATIONS

Bellman et al., "Coronary Arteriography", *New England Journal of Medicine*, vol. 262, No. 7, 2/18/60, pp. 325-328.
Ovitt et al., "Semiselective Renal Angiography", *Radiology*, vol. 119, No. 4, Dec. 1973, pp. 767-769.
Williams et al., "Coronary Arteriography", *The New England Journal of Medicine*, vol. 262, No. 7, Feb. 18, 1960, pp. 325-332.
Amplatz, "Percutaneous Arterial Catheterization and its Application", *Radiology*, vol. 87, No. 2, Feb. 1962, pp. 265-275.
Paulin, "Coronary Angiography", *Acta Radiologica*, Supplementum 233, Stockholm, 1964.

*Primary Examiner*—Stephen C. Pellegrino
*Attorney, Agent, or Firm*—Bernard, Rothwell & Brown

[57] ABSTRACT

A coronary catheter has a transverse loop at the distal end of the catheter with two spaced, outwardly directed groups of openings centered to align with blood flow to respective coronary ostia when the catheter is in a maximum radius of curvature in the aorta. Each group of openings is spaced over a region of the outer peripheral wall of the loop so as to direct a fan-like pattern of contrast medium toward the aorta wall at the situs of the corresponding coronary ostium or directly upstream therefrom.

25 Claims, 12 Drawing Figures

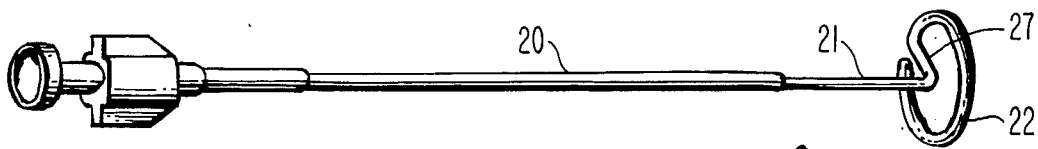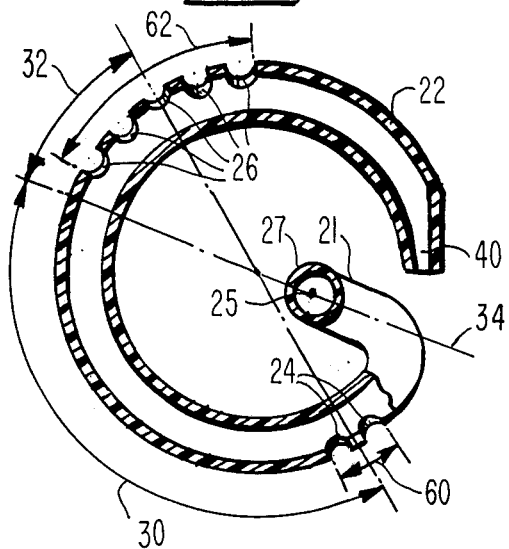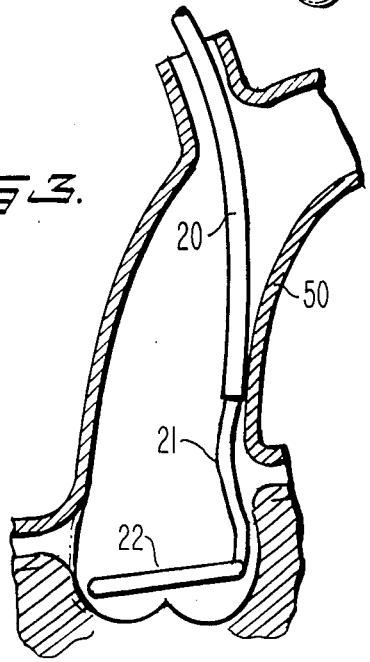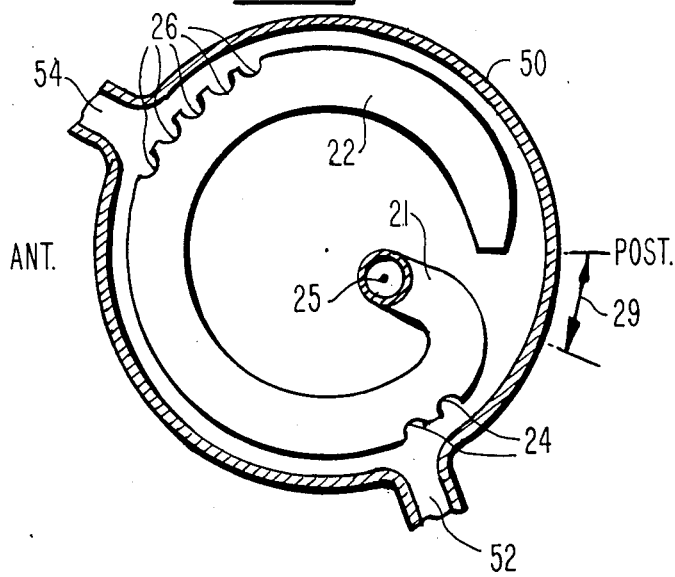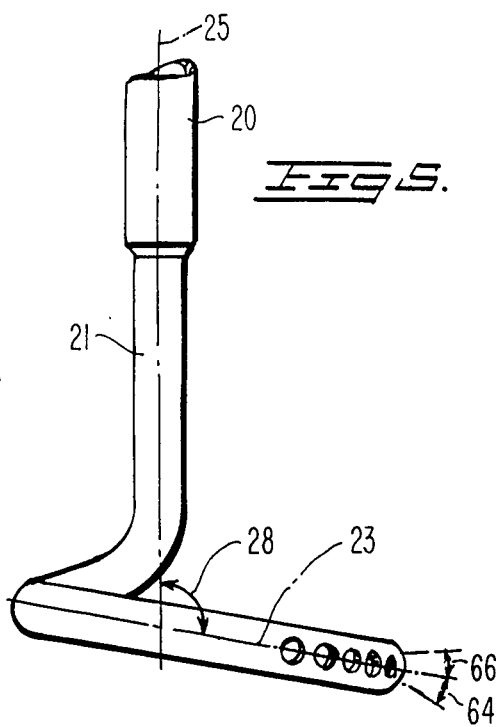

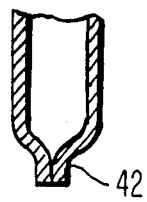
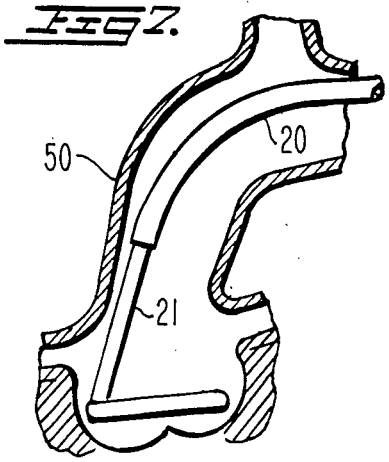
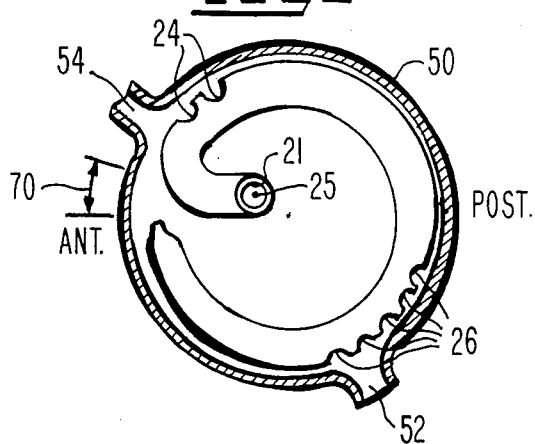
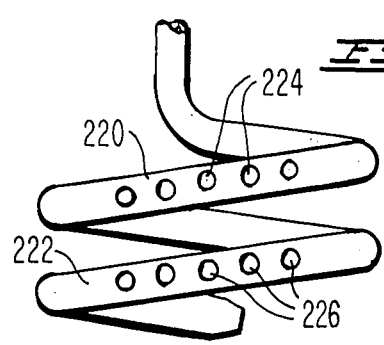
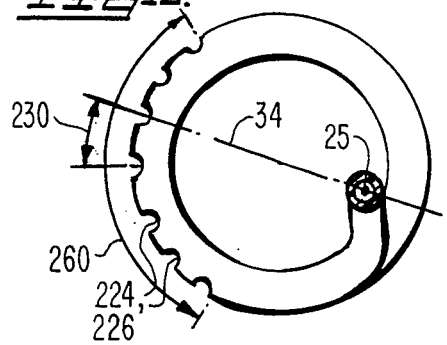
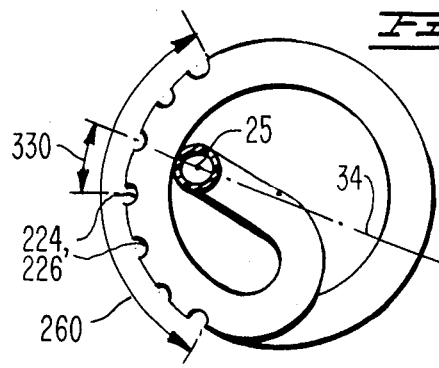
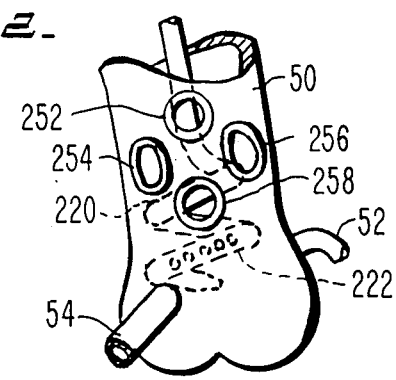

LOOP CORONARY CATHETER

This application is a continuation-in-part of copending application Ser. No 575,276 now abandoned, filed Jan. 30, 1984, which is incorporated by reference herein.

BACKGROUND OF THE INVENTION

1. Field of the Invention

The invention relates to catheters for semi-selectively injecting a radiopaque material or contrast medium into coronary arteries, including natural coronary arteries and surgically grafted bypass arteries, for radiological diagnostic purposes.

2. Description of the Prior Art

In coronary angiography, a tip of a catheter is inserted into a brachial, axillary or femoral artery and from there advanced into the portion of the aorta proximal the coronary ostia. Techniques for opacification of the coronary arteries can generally be divided into three groups, namely, (1) non-selective, (2) selective, and (3) semi-selective. In the non-selective technique, the catheter is positioned in the aorta valve cusps area which is then flooded with contrast medium, a portion of which passes into the coronary arteries. In the selective technique, the tip of a catheter is inserted directly into the ostium of each coronary artery and contrast medium is injected directly into each artery. In the semi-selective technique, a catheter tip is positioned within the aorta adjacent to the coronary ostia with one or more openings of the catheter directed toward the aorta wall so that injected contrast media is more concentrated in the outer portion of the aortic stream adjacent to the coronary ostia.

Past coronary angiography of the natural coronary arteries has been, for the most part, generally performed by successively employing two or three different catheters, the first being employed in a non-selective technique and the last one or two being employed in selective techniques. The first catheter is a generally straight catheter with an open end and a plurality of spaced sidewall openings adjacent the open end. This open end of the catheter is positioned within the aorta just above the aortic valve. Injection of contrast medium is utilized to flood the aortic cusp area and pinpoint the openings to the coronary arteries. From fluoroscopic or angiogram information gained from the first procedure, a general purpose selective catheter or successive left and right selective coronary catheters are inserted with the tip or tips being successively inserted into the corresponding left and right coronary arteries to inject contrast media therein and to enable diagnostic coronary angiograms. The selective opacification of the coronary arteries produces sharp images and pictures which are then utilized in diagnosing and treating or surgically correcting a coronary problem.

The generally employed past coronary angiography procedures have substantial deficiencies in being costly and involving considerable risk. The procedures for inserting two or three successive catheters in a leg or arm artery generally require the use of a sheath which generally must be installed in the artery under hospital operating room conditions with pre- and post-operative care. The selective catheterization of the coronary arteries has disadvantages including requiring a large amount of time to position the catheter tips in the coronary ostia, failure of the catheter to enter a coronary ostium due to a stenoic condition or an anatomical abnormality, blocking blood flow into a coronary artery to cause heart damage or malfunction such as asystole or arhythmia, creating a coronary occlusion by passing an embolus from the catheter into the coronary artery or by dislodging an arteriosclerotic plaque from the coronary wall, or otherwise damaging a coronary artery. In diagnostic coronary angiography, approximately 30% of all patients are found to have no significant coronary artery disease. There is a general need to reduce costs and risks to patients undergoing coronary angiography by employing less costly and less risky procedures. Substantial improvement could result from employment of such procedures in screening techniques to reduce the number of patients requiring the more extensive and risky procedures.

Percutaneous catheterization is less traumatic on the patient and easier to perform than procedures requiring the insertion of a sheath. In percutaneous catheterization, a needle is first inserted into the artery (brachial, axillary or femoral) and a guide wire is inserted into the vessel through the lumen of the needle. After the needle is withdrawn over the guide wire, the catheter is threaded over the guide wire into the vessel where, under fluoroscopic guidance, the tip of the catheter and guide wire are advanced into the aorta. After the guide wire is removed, withdrawal of a portion of blood to flush the catheter and controlled continuous drip of heparinization solution prevent clot insertion and formation. Where one or more additional catheters must be used, percutaneous insertion of the additional catheters into the same entry point has a high risk of creating a large tear in the artery; thus employment of a sheath is generally preferred in multiple catheter procedures.

Semi-selective catheterization including use of loop catheters has been previously studied for use in coronary arteriography, such as described in Bellman et al., "Coronary Arteriography". The New England Journal of Medicine, Vol. 252, No. 7, Feb. 18, 1960, pages 325–328; Williams et al., "Coronary Arteriography", The New England Journal of Medicine, Vol 252, No. 7, Feb. 18, 1960, pages 328–332; and Amplatz, "Percutaneous Arterial Catheterization and Its Application", Radiology Vol. 87, No. 2, February 1962, pages 265–275. These catheters have a simple loop tip in a plane at right angles to the long axis of the catheter with three side holes drilled equidistantly apart in the loop so that one hole would lie opposite each coronary sinus of Valsalva in nearly any position of catheter rotation. Contrast media is injected under pressure through the outward facing holes in the loop into portions of the aortic stream juxtamural to the coronary ostia. The obtainment of good or excellent quality angiograms were initially reported. This loop catheter technique for coronary opacification has the advantage that the catheter can be inserted into an arm or leg artery by percutaneous catheterization which can be performed by a radiologist without hospital operating conditions and with substantially less pre- and post-operative care. Also this semi-selective technique involves less risk than selective techniques due to a reduction in the possibility of the catheter blocking a coronary ostium, a reduction in the number of catheter insertions and thus a reduction in chances of clot formation and insertion, and reduction in the possibility of damaging the coronary artery or dislodging arteriosclerotic plaque.

In spite of the cost saving and the inherent greater safety of semi-selective catheterization using a coronary loop catheter, it has not achieved commercial success and has not replaced any notable portion of the employment of non-selective and selective coronary catheterization procedures. As reported by Paulin, "Coronary Angiography", Acta Radiologica, Supplementum 233, Stockholm 1964, employment of the single loop coronary catheter often failed to attain uniform opacification of both coronary arteries, and almost always showed signs of loop displacement during injection of contrast medium. The severe deficiencies of the single loop design led to the development of a double loop tip design constructed counterclockwise from the straight body portion with five side holes placed equidistantly along the periphery of the loop and which was reported to have superior stability and result in greater improved opacification of both coronary arteries. This prior double loop design, like the prior single loop design, has failed to achieve any notable commercial success.

In coronary angiography of surgically grafted bypass arteries, selective catheterization techniques are generally employed. Generally radiopaque rings are secured on the bypass vessels adjacent their connection to the aorta, and these rings are used to guide the radiologist, or cardiologist, in positioning of a selective catheter tip into the ostium of a grafted vessel, without the help of prior non-selective opacification. The selective catheterization of bypass arteries also has a higher risk of blocking the artery and requires more time for catheter placement than a semi-selective technique.

A recent radiology development concerns the increasing employment of computerized radiology techniques including digital subtraction angiography (DSA) wherein arterial images taken during injection are enhanced by subtraction techniques. Subtraction of base image portions enables the production of sharp high contrast angiograms electronically on a cathode ray tube with the employment of less contrast medium and less exposure to X-rays than has been possible in the production of film images by direct X-ray exposure. However, DSA has thus far been unable to effectively image the natural coronary arteries with intravenous and non-selective low volume aortic root injection. In the latter situation the contrast delivery is particularly inefficient as most of the injected contrast medium is immediately washed out by the ascending aorta flow.

SUMMARY OF THE INVENTION

The present invention is summarized in a coronary catheter for angiography having a loop formed on its distal end portion extending in a plane transverse to the axis of the catheter and parallel to the plane of the coronary ostia with one or more opening means formed in the outer peripheral wall of the loop portion. In one aspect of the invention, each opening means extends longitudinally along the peripheral w;all of a sector of the loop, such as a plurality of closely spaced holes, to produce a fan-like pattern of injection selected to account for small anatomical abnormalities or small misalignments. In a second aspect of the invention, the opening means is located on the loop so as to align with blood flow to a corresponding coronary ostium when the catheter body has a maximum radius of curvature in the aorta.

An object of the invention is to produce a loop type catheter for coronary angiography which, in a relatively simple procedure, can produce acceptable opacification of a coronary artery in order to eliminate a substantial portion of the requirement for multiple catheterization and selective catheterization.

Another object of the invention is to reduce the risk to patients undergoing coronary diagnosis by catheter injection of radiopaque material.

A still further object of the invention is to enable the development of lower cost outpatient or office procedures for coronary angiography.

One advantage of the invention is that fan-like injection patterns overcome most misalignment and anatomical abnormality problems causing opacification failure in semi-selective coronary catheterization.

Another advantage of the invention is that the bias of the catheter stem to assume the greatest possible radius of curvature in the aorta is utilized to maintain alignment of openings in a transverse loop tip with coronary ostia.

One further feature of the invention is that the employment of periphery openings in only two spaced sections of the circumference of the loop results in concentration of the contrast medium injection from such sectors.

Other objects, advantages and features of the invention will be apparent from the following description taken in conjunction with the accompanying drawings.

BRIEF DESCRIPTION OF THE DRAWINGS

FIG. 1 is a perspective view of a loop coronary catheter in accordance with the invention.

FIG. 2 is a plan view, partially in cross-section, of a loop portion of the catheter of FIG. 1.

FIG. 3 is an elevational cross-section view of the stem of an aorta illustrating placement of the catheter variation of FIG. 2 by a brachial or axillary approach.

FIG. 4 is a horizontal cross-section view of the aorta illustrating the placement of the catheter of FIGS. 2 and 3.

FIG. 5 is a side view of the loop of FIG. 2.

FIG. 6 is a cross-section view of a modified end portion of the catheter of FIG. 2.

FIG. 7 is an elevational cross-section view of an aorta stem illustrating placement of the catheter variation of FIG. 2 by a femoral approach.

FIG. 8 is a horizontal cross-section view of the aorta showing placement of the catheter variation of FIG. 7.

FIG. 9 is an elevation view of a modified loop coronary catheter in accordance with the invention.

FIG. 10 is a plan view of a loop portion of the catheter of FIG. 9.

FIG. 11 is a plan view of a variation of the catheter of FIGS. 9 and 10.

FIG. 12 is a front elevational view of an aorta stem illustrating, in dashed lines, the employment of the catheters of FIGS. 9–11.

DESCRIPTION OF THE PREFERRED EMBODIMENTS

As shown in FIG. 1, a catheter, in accordance with one embodiment of the invention, has a generally straight body portion 20 with a distal end portion 21 in which is formed a loop 22 with its plane 23, FIG. 5, transverse the axis 25 of the body portion 20 so as to extend in a plane generally transverse the aortic root below the coronary ostia, see FIG. 3. Openings 24 and 26, FIGS. 2 and 4, are selectively formed and positioned in the peripheral outer wall of the loop 22 for semi-selectively directing contrast medium in the aorta stem. The openings 24 and 26 are respective groups of closely spaced round holes, slots (not shown), or other opening means which extends or is spaced along the loop periphery for circumferential distances at least two times the width of the opening means. The positions of the openings 24 and 26 on the loop 22 are selected relative to the offset of the axis 25 from the center of the loop 22 so as to align with blood flow to coronary ostia when the catheter body 20 assumes a maximum radius of curvature in the aorta.

The catheter is constructed from a suitable plastic tubing stock such as singly extruded, coextruded, or braided catheter tubing. The body portion 20 is selected to give the catheter the desired torque and column strength necessary to push and rotate the catheter while inserting and placing the catheter in position. The body portion 20 is shown as being straight, but curvatures may be formed therein to aid in insertion and/or positioning of the catheter. Preferably the tip portion 21 is softer and more flexible; suitable softer tip portions can be formed by fusing a section of softer plastic tubing onto the body portion, extending the end of a more flexible outer tube past the distal end of a more rigid inner tube on which the outer tube is drawn or coextruded, or forming the tip portion with less wall thickness or without reinforcement to render it more flexible. The outside diameter of the catheter tubing is generally in the range from 4 to 10 French (1.32 to 3.3 mm) with an inside diameter selected from the range of 0.7 to 3.0 mm (0.030 to 0.120 inch); a body portion 21 with an outside diameter of about 7 French (0.090 inch) (2.30 mm) and an inside diameter of about 0.061 inch (1.55 mm) and a tip portion 21 with an outside diameter of about 0.068 inch (1.73 mm) and an inside diameter of about 0.048 inch (1.22 mm) is preferred. The total length of the catheter is generally in the range from 50 to 120 cm, and preferably about 65 cm for a brachia or axillary approach or about 115 cm for a femoral approach. The tip portion 21 is preferably about 12 cm long.

The loop 22 is generally circular with a diameter in the range from 0.5 to 4 centimeters, and preferably about 2.8 centimeters. The origin 27 of the loop 22 beginning at the axis 25 of the stem 20 can be displaced toward the center of the loop 22 as shown in FIGS. 1 and 2, or can extend directly from the loop 22 as shown in FIG. 3. The loop 22 is illustrated as extending clockwise, but can extend counterclockwise. The cross-sectional diameter of the end 40 of the loop is reduced to form a restricted opening or a reduced lumen as shown in FIG. 2. Alternatively, a closed end 42, FIG. 6, can be substituted for the reduced lumen end 40. The open end 40 is employed where the catheter is inserted over a guidewire into an artery (percutaneous catheterization), and the closed end 42 can be employed where the catheter is inserted through a sheath into the artery. The size of the opening in the end 40 is selected to be large enough to easily slip over a conventional guidewire, e.g., about 0.87 mm in diameter, but to restrict the flow of contrast medium through the end and thus produce substantial flow through the openings 24 and 26. The angle 28, FIG. 5, that the plane 23 of the loop makes with the axis 25 of the catheter body is selected within the range from 80° to 120°. The preferred angle 28 is about 110°.

The openings or groups of holes 24 and 26 are positioned selectively in the loop 22 so that, when the body portion 20 assumes a maximum radius of curvature in the aorta, i.e., when the axis 25 of the body portion 20 is offset in the outermost position from the center of the loop 22 relative to the aorta curvature, the groups of holes 24 and 26 are aligned with the coronary ostia or with aorta wall sectors over which aortic flow passes to the coronary ostia. As shown in FIGS. 3 and 4 for a catheter inserted through the brachial or axillary artery, the resilience of the straight body portion 20 urges the catheter body to a maximum radius of curvature where the lower end of the catheter body or stem 20 is positioned along the posterior wall at an angle 29, centered at the axis of the loop 22, in the range of 10° to 30° or about 20° to the left of the center (sagittal plane) of the posterior wall of the aorta stem 50. As shown in FIGS. 2 and 4, the groups of holes 24 and 26 are centered at respective angles 30 and 32 centered at the loop axis from a plane 34 which contains the axis 25 and bisects the loop 22. The angles 30 and 32 extend in opposite directions from the point of intersection of the plane 34 with the loop 22 opposite to beginning of the loop 22 at the base of the catheter stem 20 so that the groups of holes 24 and 26 are centered in alignment with respective blood flows to left and right coronary ostia 52 and 54 when in their most commonly found positions The angle 30 is generally in the range from 120° to 165° while the angle 32 is generally in the range from 5° to 45°; angles in the ranges of 140°–160° and 20°–40° are preferred for the respective angles 30 and 32. For the brachial or axillary approach, the optimum angles 30 and 32 are believed to be 155° and 25°, respectively.

It is noted that the centers of the groups of holes 24 and 26 are about 180° apart and that these centers are displaced angularly from a reported most common angular position of the coronary ostia. Clinical testing, using the hereinafter described femoral approach with loops positioned in the aortic root and with varying numbers and angular positioning of openings, has demonstrated that such angular displacement produces optimized opacification of the coronary arteries. This is believed to be due to swirling of the blood in opposite directions from the posterior wall.

The holes in the groups 24 and 26 are spaced over arcuate sections of the loop extending through respective angles 60 and 62 in order to account for most anatomical variations in ostia positions and to account for some misalignment of the catheter. Arcuate loop sectors, which are devoid of wall openings extend through angles substantially greater than the angles 60 and 62 to separate and extend on either side of each of the sectors 60 and 62. These sectors without openings reduce the amount of contrast medium being injected and concentrate the injected contrast medium in regions aligned with the coronary ostia. The number of the holes in each group 24 and 26 is selected from the range of two to six. The number or the size of the holes in the more distal group 26 is preferably greater than the number or size of holes in the more proximal group 24. Selection of larger sized holes and/or a greater number of holes in the more distal group 26 accounts for a drop in pressure within the loop between the holes 24 and 26 as well as producing a wider discharge angle to insure opacification of coronary arteries which are anatomically displaced from a normal position. The holes in each group 24 and 26 have sizes and spacing so as to produce web or fan-like flows, such as streams in a fan-like configuration, of contrast medium from the holes 24 and 26 toward or over the regions of the aorta wall where blood flow passes enroute to the coronary ostia wherein the contrast medium is sufficiently uniform throughout each fan-like flow to ensure that any coronary ostia aligned with any portion of the flow will receive substantial amounts of contrast medium to insure adequate concentration of contrast medium entering the coronary ostia to opacify the coronary arteries. Generally the plurality of holes 24 extent over a circumferential sector or angle 60 of 10° to 40°, preferably about 10°-30°. Generally the plurality of holes 26 extend over a circumferential sector or angle 62 of 10° to 75°, preferably about 45°-65°. As an example for a 7 French catheter with a tip lumen diameter of 1.2 mm, 2 round holes 24 of 1.0 mm diameter evenly spaced over an angular segment 60 of 20°, and 5 round holes 26 of 1.0 mm diameter evenly spaced over an angular segment 62 of 55° are suitable.

The loop 22 being of generally circular configuration, can be considered as having four arcuate portions of about 90° wherein the first arcuate portion extending from the origin 27 includes the peripheral wall opening means 24, the second arcuate portion is free of any peripheral wall opening means the third arcuate portion which is opposite the first arcuate portion includes the peripheral wall opening means 26, and the fourth arcuate portion is free of peripheral wall opening means. The second and fourth arcuate 90° portions are opposite each other.

Each of the holes 24 and 26 is directed outwardly in the periphery of the loop 22 so that contrast medium discharged therefrom is directed toward the wall of the aorta. The direction of the openings can be selected within a range generally from about 20° below the plane 23, see angle 64 in FIG. 5, to 5° above the plane 23, see angle 66. Preferably the openings 24 and 26 are directed within a range from 5° below the plane to a direction along the plane 23 perpendicular to the axis 25 of the catheter stem.

Inserting of the catheter by a femoral artery approach is illustrated in FIGS. 7 and 8. Optimum angles 30 and 32 for this approach are found to be 150° and 30°, respectively, based upon clinical testing. The femoral approach results in the lower end of the catheter stem 20 being positioned along the anterior wall at an angle 70 centered at the axis of the loop 22, in the range of 5° to 25° or about 15° to the right of the center (sagittal plane) of the anterior wall of the aorta stem 50 when the catheter body 20 is at its maximum radius of curvature in the aorta. The openings 24 and 26 in this approach align with the blood flows to the coronary ostia 54 and 52, respectively.

In a modified catheter of FIG. 9 designed for opacifying bypass coronary arteries, a double loop tip with an upper loop 220 and a lower loop 222 is formed on the catheter in place of the single loop. Openings or groups of outwardly directed holes 224 and 226 are formed in the respective upper and lower loops 220 and 222 in coextending angular portions or sectors of the loops. As shown in FIGS. 10 and 11, the holes are spaced in angular portions extending for an angle 260 which is preferably about 120°. For the brachial or axillary approach, FIG. 10, the openings or groups of holes 224 and 226 are centered at an angle 230 generally within the range of 10° to 30° and preferably about 20° from the plane 34 and its intersection with the loops 220 and 222 opposite the stem 20. For the femoral approach, FIG. 11, the openings 224 and 226 are centered at an angle 330 generally within the range of 5° to 25° and preferably about 15° from the axis of the catheter stem. As shown in FIG. 12, the ostia 252, 254, 256 and 258, created surgically for bypass arteries, generally are within the anterior one-third portion of the aorta stem, and the openings 224 and 226 and loops 220 and 222 are positioned to semi-selectively opacify these bypass arteries.

The catheters of FIGS. 9-12 are illustrated with a double loop tip for semi-selectively opacifying quadruple bypass arteries. Alternatively a catheter with a single loop having a single group of holes positioned in accordance with FIGS. 10 or 11 may be employed to opacify a lesser number of bypass arteries, or the illustrated quadruple bypass arteries. In a still further alternative, a catheter can include a distal loop in accordance with FIG. 2 together with one or more additional loops in accordance with FIGS. 10 or 11 to opacify both the natural coronary arteries and the bypass arteries.

In employment of the above catheters, conventional catheterization such as percutaneous catheterization or sheath catheterization is employed to place the loop or loops of the catheter in the root region of the aorta. A small amount of contrast medium is injected by hand to fill and opacify the catheter and to aid in final positioning of the catheter loops under fluoroscopic guidance. The loop of the catheter is positioned at a level at least equal to and preferably below the coronary ostia so that injected contrast medium from the groups of holes is directed into the coronary ostia or into a portion of the aorta flow passing directly to the coronary ostia. Since the group or groups of peripheral holes, see 24, 26, 224, or 226, are positioned on the loop or loops so as to align with blood flow to the corresponding coronary ostia when the stem or body portion 20 assumes a maximum radius of curvature in the aorta, the final positioning of the catheter is made substantially easier in that the resilience of the catheter body biases the catheter to a normal aligned position, and, only in exceptional circumstances of anatomical abnormality, will the catheter have to be rotated against the bias.

Once the catheter is properly positioned, contrast medium such as 30% Renografin is injected, either by power injection or manually, at a rate within the range from 2 to 10 cc/sec. over a period in the range from 1 to 3 seconds. Angiograms are taken at a rate of 5 or 10 per second during the injection and for a short period thereafter. Preferably the angiograms are taken by digital subtraction angiography (DSA) equipment to enable use of lower injection rates and lower contrast medium concentration to reduce any possible problems associated therewith. Injection and angiogram exposure can be controlled by ECG gating; for example, the R wave can be utilized to produce contrast medium injection during a period beginning at the later part of systole and covering the next two distole periods and intervening systole.

Tests conducted on canine subjects using both direct film exposure and DSA techniques and clinical tests on human subjects have shown that the present catheter can produce angiograms that are greatly superior to those produced by non-selective techniques where a conventional pigtail catheter is used to flood the aorta root with contrast medium, and that are nearly equivalent to results obtained using selective techniques Further, studies comparing image acquisition with and without ECG gating have been done demonstrating excellent motion stopping with the gating.

The present loop coronary catheter produces substantially improved results in angiography compared to the prior art loop coronary catheters. This improvement is attributable, at least partly, to (1) the present employment of a group of holes spaced within an arcuate sector of the loop as opposed to the prior art use of a single hole, (2) the selective positioning of openings or groups of holes so that each group will be aligned with blood flow to a corresponding coronary ostia when the catheter stem assumes a maximum radius of curvature in the aorta, and (3) the positioning of openings only in sectors of the loop corresponding to coronary ostia. The use of plural holes extending through a substantial angular sector of the loop results in a web or fan-like injection of contrast medium to insure that the contrast medium enters each coronary artery when small anatomical abnormalities and small misalignments would cause injection from single holes to miss the coronary ostium. The positioning of the openings so as to be aligned with blood flows to the coronary ostia when the catheter stem assumes a maximum radius of curvature in the aorta results in the catheter havin9 substantial resistance against moving away from such alignment; otherwise the force of the injection of contrast medium can easily move the loop to cause misalignment and failure to adequately opacify the coronary arteries. The placement of peripheral openings in only sectors of the loop corresponding to blood flow to coronary ostia leaving the periphery of other sectors closed results in increased contrast flow from the openings of selected sectors to further enhance flow of contrast medium into coronary arteries. The prior art loop coronary catheters depended more upon flooding the aorta cusp region (non-selective catheterization) rather than producing direct injection of a stream of contrast medium at the coronary ostia, or at an aorta wall portion over which flow passes directly to the coronary ostium. Employment of DSA, further enabling angiography with less contrast medium flow, contributes to the stability of the catheter loop during injection as well as increasing angiogram contrast.

Since many modifications, variations and changes in detail may be made to the above-described embodiments without departing from the scope and spirit of the invention, it is intended that all matter in the foregoing description and shown in the accompanying drawings be interpreted as illustrative and not in a limiting sense.

What is claimed is:

1. A catheter for coronary angiography comprising
a tubular flexible body portion,
a tubular flexible tip portion on one end of the body portion communicating therewith,
said tip portion having a loop formed therein with the plane of the loop being transverse to the asxis of the body poriton,
said loop having at least one arcuate portion with outwardly directed peripheral opening means formed therein,
said periperhal opening meansextending longitudinally in the peripheral wall of the one arcuate portion for a distance at leat two times the width of the opening means for directing a fan-like flow of contrast medium toward a selected sector of an aorta wall, and
said loop having adjacent arcuate portions devoid of peripheral openings on both sides of the one arcuate portion and extending for angular distances each greater than the angular distance of the one arcuate portion.

2. A catheter as claimed in claim 1 wherein the center of the loop is offset relative tothe axis of the body portion and one arcuate portion is positioned on the loop so as to align in the distance of aortic flow to a coronary ostium when the catheter body portion is positioned with a maximum radius of curvature in an aorta.

3. A catheter as claimed in claim 1 wherein the outwardly directed peripheral opening means includes a plurality of holes closely spaced longitudinally along the peripheral wall of the one arcuate portion of the loop.

4. A catheter as claimed in claim 1 wherein the opening means extends along the one arcuate portion for an angle in the range from about 10° to 75° centered on the axis of the loop.

5. A catheter as claimed in claim 3 wherein the plurality of holes are spaced over an angle in the range from 10° to 75° centered on the axis of the loop.

6. A catheter as claimed in claim 5 wherein the one arcuate loop portion contains at least five holes.

7. A catheter as claimed in claim 1 wherein the loop of the catheter consists substantially of a single loop extending around a center which is offset relative to the axis of the body portion; and includes two and only two spaced, outwardly directed, peripheral opening means each extending longitudinally over a peripheral wall of the loop for a distance at least two times the width of each opening means and being positioned so as to align in the direction of aortic flow to respective coronary ostia when the body portion of the catheter is positioned with a maximum radius of curvature in an aorta.

8. A catheter as claimed in claim 7 wherein the two opening means each include a plurality of substantially round holes closely spaced longitudinally along the peripheral wall of the loop.

9. A catheter as claimed in claim 7 wherein the two opening means are centered at respective opposite angles centered at the axis of the loop and within the range from about 5° to 45° and from about 120° to 165°, respectively, from a plane bisecting the loop and containing the axis of the body portion.

10. A catheter as claimed in claim 9 wherein the respective opposite angles are in the ranges of about 20° to 40° and 140° to 160°, respectively.

11. A catheter as claimed in claim 9 wherein the catheter is designed for insertion through a femoral artery, and the opposite angles are about 30° and 150°, respectively.

12. A catheter as claimed in claim 9 wherein the catheter is designed for insertion through an artery in an arm, and the opposite angles are about 25° and 155°, respectively.

13. A catheter as claimed in claim 7 wherein the opening means in the more distal portion of the loop has a cross-sectional area which is greater than the opening means closer to the body portion.

14. A catheter as claimed in claim 13 wherein the opening means in the more distal portion of the loop is formed by a plurality of openings spaced over an angle in the range from 45° to 65° centered on the axis of the loop and the opening means in the more proximal portion of the loop is formed by a plurality of openings spaced over an angle in the range from 10° to 30° centered on the axis of the loop.

15. A catheter as claimed in claim 1 wherein the catheter is designed for opacifying bypass arteries; the tip portion includes a helix with a pair of loops transverse to the axis of the body portion; and the pair of loops each contain one arcuate portion with outwardly directed peripheral opening means formed therein, and adjacent arcuate portions devoid of peripheral openings of either side of each one arcuate portion and extending for angular distances each greater than the angular distance of the one arcuate portion.

16. A catheter as claimed in claim 15 wherein each one arcuate portion is positioned on the respective loop so as to align in the direction of aortic flow with a bypass artery ostium when the catheter body portion is positioned with a maximum radius of curvature in an aorta.

17. A catheter as claimed in claim 15 wherein each opening means includes a plurality of holes closely spaced longitudinally throughout the one arcuate portion of the loop.

18. A catheter as claimed in claim 17 wherein each plurality of holes are spaced through an angle of about 120°.

19. A catheter for coronary angiography comprising a tubular flexible body portion, a tubular flexible tip portion on one end of the body portion and communicating therewith, said tip portion having a loop formed therein with the plane of the loop being transverse to the axis of the body portion and with the center of the loop being offset relative to the axis of the body portion, said loop consisting of four arcuate portions of about 90°, two outwardly directed opening means formed in the peripheral wall of two corresponding opposite arcuate portions of the four arcuate portions with the other two opposite arcuate portions being free of any peripheral opening, and said two outwardly directed opening means being formed in the outer peripheral wall at positions selected relative to the axis of the body portion so that said two opening means align with blood flows to a respective normally positioned coronary ostia when the body portion is in a maximum radius of curvature within the aorta.

20. A catheter as claimed in claim 19 wherein the two opening means are centered at respective opposite angles within the ranges from about 5° to 45°, and from about 120° to 165°, respectively, from a plane bisecting the loop and containing the axis of the body portion.

21. A catheter as claimed in claim 20 wherein the two opening means are centered at angles in the ranges of about 20° to 40° and 140° to 160°, respectively, from the plane bisecting the loop.

22. A catheter as claimed in claim 20 wherein the catheeter is designed for insertion through a femoral artery, and the opposite angles extend from the axis of the body portion of about 30° and 150°, respectively.

23. A catheter as claimed in claim 20 wherein the catheter is designed for insertion through an artery in an arm, and the opposite angles extend from an intersection of the bisecting lane with the loop opposite to the junction of the loop with the body portion of about 25° and 155°, respectively.

24. A catheter as claimed in claim 19 wherein the opening means in the more distal portion of the loop has a cross-sectional area which is greater than the opening means closer to the body portion.

25. A catheter as claimed in claim 24 wherein the opening means in the more distal portion of the loop is formed by a plurality of openings spaced over an angle in the range from 45° to 65°, centered on the axis of the loop, and the opening means in the more proximal portion of the loop is formed by a plurality of openings spaced over an angle in the range from 10° to 30° centered on the axis of the loop.

* * * * *